United States Patent [19]

Seifert

[11] Patent Number: 5,100,028
[45] Date of Patent: *Mar. 31, 1992

[54] PRESSURE-RUPTURABLE CONTAINER SEAL HAVING A FLUID FLOW DIRECTING SHIELD

[75] Inventor: Robert P. Seifert, Wolfeboro, N.H.

[73] Assignee: Institute Guilfoyle, Belmont, Mass.

[*] Notice: The portion of the term of this patent subsequent to Jul. 30, 2008 has been disclaimed.

[21] Appl. No.: 620,280

[22] Filed: Nov. 30, 1990

Related U.S. Application Data

[63] Continuation-in-part of Ser. No. 402,084, Sep. 1, 1989, Pat. No. 5,035,348.

[51] Int. Cl.⁵ .............................................. B65D 47/10
[52] U.S. Cl. .................................. 222/107; 222/189; 222/541; 222/564
[58] Field of Search ............... 222/92, 107, 541, 189, 222/491, 212, 213, 564; 206/219; 401/132

[56] References Cited

U.S. PATENT DOCUMENTS

| | | | |
|---|---|---|---|
| 2,430,995 | 11/1947 | Roos | 222/107 |
| 2,663,461 | 12/1953 | Brown | 222/107 |
| 3,334,790 | 8/1967 | Eaton | 222/107 |
| 3,601,252 | 8/1971 | Sager | 222/107 |
| 3,757,782 | 9/1973 | Aiken | 222/107 X |
| 3,913,789 | 10/1975 | Miller | 222/107 |
| 3,964,604 | 6/1976 | Prenntzell | 206/219 |
| 4,027,985 | 6/1977 | Loesser, III | 222/106 |
| 4,759,472 | 7/1988 | Strenger | 222/541 |
| 4,890,744 | 1/1990 | Lane, Jr. et al. | 222/107 |
| 5,035,348 | 7/1991 | Seifert | 222/541 X |

FOREIGN PATENT DOCUMENTS 0078761 5/1983 European Pat. Off. ............ 222/541

*Primary Examiner*—Kevin P. Shaver
*Attorney, Agent, or Firm*—Cesari & McKenna

[57] ABSTRACT

A flexible fluid dispenser includes a flexible fluid-containing vessel which has a seal which seals a top wall of the vessel to a bottom wall and is shaped to concentrate in a region thereof forces resulting from pressure generated by applying a force to the dispenser. The dispenser further includes a shield shaped to direct fluid released from the dispenser in a desired direction. When a sufficiently large force is applied to the dispenser, the weaker top or bottom wall of the vessel ruptures, or opens, at the concentration region of the seal. The released fluid is then directed by the shield in the desired direction.

11 Claims, 2 Drawing Sheets

PRESSURE-RUPTURABLE CONTAINER SEAL HAVING A FLUID FLOW DIRECTING SHIELD

This application is a continuation-in-part of Ser. No. 07/402,084 filed Sept. 1, 1989, now U.S. Pat. No. 5,035,348.

FIELD OF INVENTION

This invention relates generally to fluid dispensers, and more particularly to disposable, flexible fluid dispensers.

BACKGROUND OF THE INVENTION

Disposable, flexible plastic or glass fluid dispensers are currently used to dispense all sorts of liquid, or liquid-like, substances. For example, take-out food restaurants offer ketchup and mustard to their customers in disposable plastic dispensers which resemble rectangular pouches, and cosmetic manufacturers offer their customers one-application samples of various products such as shampoo, moisturizer, etc., in disposable plastic or glass dispensers. Similarly, pharmaceutical companies distribute medications, such as liquid vitamins or ointments, in disposable one-dosage dispensers.

The user opens the dispensers by splitting, cutting or puncturing them. Depending on the design of the dispenser, the user may open it by cutting or ripping off a particular section of it, typically along a perforation, puncturing it with a sharp object, or squeezing it until it pops open. Often, when a user rips the dispenser along a perforation, he or she simply pulls off a section of the dispenser without opening it. The user then must squeeze the dispenser to further split it, all the while hoping that the contents of the dispenser do not spray out in all directions through the perforations.

A user who attempts to open a dispenser by puncturing it may end up spewing the contents in unpredictable and often uncontrollable directions. For example, a user attempting to puncture a dispenser at a particular spot may inadvertently squeeze the dispenser with enough force to split it at a different, and often unexpected, spot. The contents of the dispenser may then spill out through the split. Many take-out food customers share the experience of inadvertently splitting a ketchup dispenser and spilling the ketchup all over themselves. If, instead of ketchup, the dispenser contains a liquid medication or a reactive chemical, the consequences of spraying the contents may be serious. What is needed is a disposable dispenser which opens at a predictable spot in a predictable manner.

The unpredictable dispensers present users with a second, related problem, namely, the problem of controlling the amount of liquid which emerges from the dispenser once it is opened. For example, when a user squeezes a dispenser to open it, he or she may squeeze with enough force to cause a relatively large amount of fluid to spurt out of the dispenser through the opening. Similarly, once the dispenser is opened, a later squeeze may result in the dispensing of a large amount of the fluid when the person squeezing the dispenser requires only a small amount. What is needed is a dispenser which releases its liquid contents in a controllable manner.

SUMMARY

The invention is a flexible fluid dispenser which includes a seal which is shaped to focus, in a region thereof, forces generated inside the vessel when pressure is applied to the vessel exterior. The vessel wall in this force-focusing region ruptures when sufficient force is applied to the vessel, and the remainder of the seal remains intact. Accordingly, when a user squeezes the vessel to open it, the vessel opens, or ruptures, at the force-focusing seal in the region of the seal in which the force is focused. The vessel thus has a predictable failure point.

In a first embodiment, the vessel includes at one end an inwardly-pointing "V-shaped" seal. The apex of the V-shaped seal points toward the center of the vessel. When a user squeezes the vessel to open it, the resulting forces generated inside the vessel are focused at the apex of the inwardly-pointing V-shaped seal. The focused pressure shears the vessel wall, at the apex, to create an opening which is approximately the size of the apex. When the vessel wall opens, the pressure in the vessel is released, and the vessel contents may be poured or forced out through the opening.

Another dispenser embodying the invention includes a force-focusing seal which has a periphery which is smaller than the periphery of the vessel at the same location. The seal thus focuses forces generated in the vessel over the area of the seal. When a user squeezes this vessel to open it, the vessel wall ruptures at the force-focusing seal, and the opening is approximately the size of the seal.

A shield ma be attached to the vessel to direct the fluid released from the vessel in a particular direction. A shield is particularly useful when the vessel houses sterile or toxic fluids, because a user need not come in contact with the fluid to direct it to a desired target.

The various seals may be formed using any conventional sealing method. However, ultra-sonic sealing is the preferred method of forming the force-focusing seal. To form this seal, a sealing mechanism presses together corresponding sections of each side of the vessel between dies configured to shape the seal as desired. The sealing mechanism then applies to the vessel sufficient energy to cause the vessel walls between the dies to vibrate and heat. The vessel material melts and, when the energy is no longer applied, the vessel walls fuse together to form the seal.

The material on the side to which the energy is applied melts more than the material on the other side. Accordingly, one side of the vessel flattens and thins more than the other, and the seal thus has one side which is weaker than the other. When a user squeezes the vessel to open it, the weaker seal wall ruptures. The pressure in the vessel is then released, through the opening, and the remainder of the seal and the vessel walls remain intact.

BRIEF DESCRIPTION OF THE DRAWINGS

For a more complete understanding of the features, advantages, and objects of the invention, reference should be made to the following detailed description and the accompanying drawings, in which.

DETAILED DESCRIPTION

Figure 1:
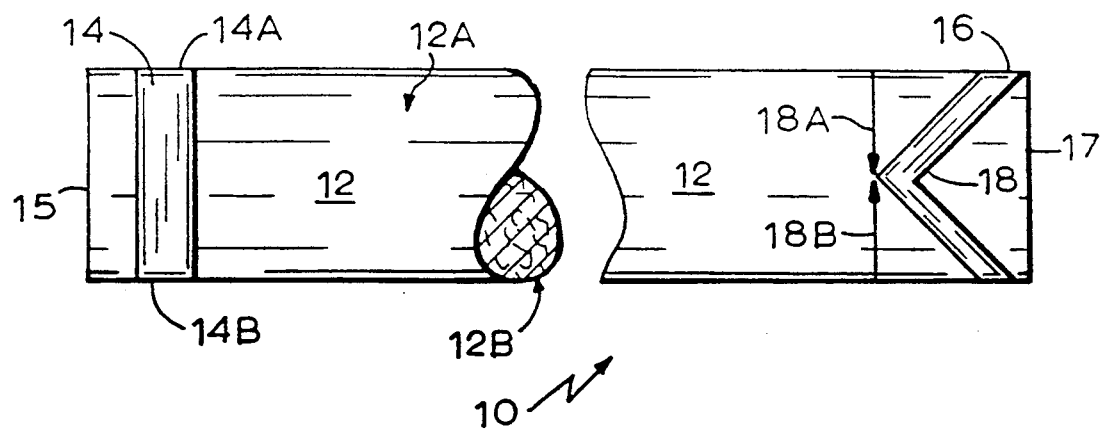
FIG. 1 is an illustration of a dispenser constructed in accordance with a first embodiment of the invention.

As shown in FIG. 1, a dispenser 10 constructed in accordance with a first embodiment of the invention includes a vessel 12 having a substantially linear seal 14 at an end 15 and an inwardly-pointing "V-shaped" seal 16 at an opposite end 17. The inwardly-pointing V-shaped seal 16 is oriented such that the seal apex 18 points toward the substantially linear seal 14. The dispenser 10 is made of a relatively flexible substance, for example, a plastic such as polyethylene.

The seals 14 and 16 may be formed using any conventional sealing technology. However, a preferred method of forming the seal is to use an ultra-sonic sealer. The sealer uses dies in the shape of the desired seal to apply pressure to a top side and a bottom side of the vessel, that is, the sealer presses together the portions of the vessel walls it is to seal. The sealer then applies ultrasonic energy, through one of the shaped dies, to the seal area. The resulting heat causes the pressurized wall sections to adhere. When the energy is no longer applied, the seal immediately cools and the dies are removed.

In order to store liquid in the dispenser 10, the vessel 12 is first sealed at one end, for example, end 17, using appropriately shaped dies. Next, the vessel 12 is filled with liquid and the open end 15 of the vessel 12 is sealed.

The ultimate characteristics of the material contacted by the die to which the energy is applied differ from those of the material contacted by the opposing die. Accordingly, the seal has one side which is weaker than the other side. Thereafter, when sufficient pressure is applied to the vessel to open it, it is this weaker side of the vessel which opens, or ruptures, at the seal.

The overall structure of the dispenser 10, and more particularly the inwardly-pointing V-shaped seal 16 on one end, results in the dispenser 10 opening predictably at apex 18. When the user squeezes the dispenser 10, the resulting stresses are distributed over the walls of the vessel and the seals 14 and 16. The forces to which linear seal 14 is subjected act on one side of the seal, while, as a result of the geometry of the V-shaped seal, the stresses to which seal 16 is subjected act on two sides of the seal. At a region of the seal away from the apex, the forces act separately on each side of the seal. At the apex, however, the sides of the seal are close together and the forces are essentially additive, which subjects the apex 18 to greater stress than any other part of the seal 16. This stress cause the vessel wall to shear, or rupture, at the apex 18.

The force required to open the dispenser 10 varies depending on the size and shape of the dispenser 10, the material out of which the dispenser is constructed and the area of the seal at the tip of the apex. However, before a user squeezes the dispenser 10 he or she knows where the dispenser 10 will open. Once the vessel wall opens the forces in the vessel are released. Thus the vessel wall opening remains the size of the force-focusing part of the seal. A user may then apply additional pressure to the vessel to force the fluid from it without further rupturing the vessel wall.

The seal 14 may be of any shape, as long as it is positioned to have the internal forces acting only on one of its sides. For example, the seal 14 may be "C-shaped", or it may be V-shaped With its apex pointing away from the center of the vessel.

The various seals may be formed using any conventional sealing method with the same result, which is that the dispenser 10 opens at the apex 18. However, if a dispenser is to house oily fluids, ultra sonic sealing is the preferable method of sealing. The ultra sonic sealing method forces the fluid from between the two sides of the vessel using a combination of the pressure of the dies pressing against each other and the vibrations in the vessel walls at the seal location caused by the application of energy to on of the dies. The pressure/vibration combination forces all traces of the oily fluid away from the seal location and enables the vessel walls to seal firmly together. Heat sealing, for example, may not force all of the oily fluid from the seal location, and the residual fluid then inhibits the walls from adhering to each other and forming a proper seal.

If the side on which the dispenser opens is important to the user, conventional methods of rendering on side of the vessel weaker than the other at the seal may be used to ensure that the failure point is on a particular side of the dispenser. For example, the material on one side of the dispenser may be thinner than the material on other, at least in the region of the seal. Then, when pressure is applied to the vessel the thinner, and thus, weaker, side ruptures at the force-focusing seal.

Figure 2:
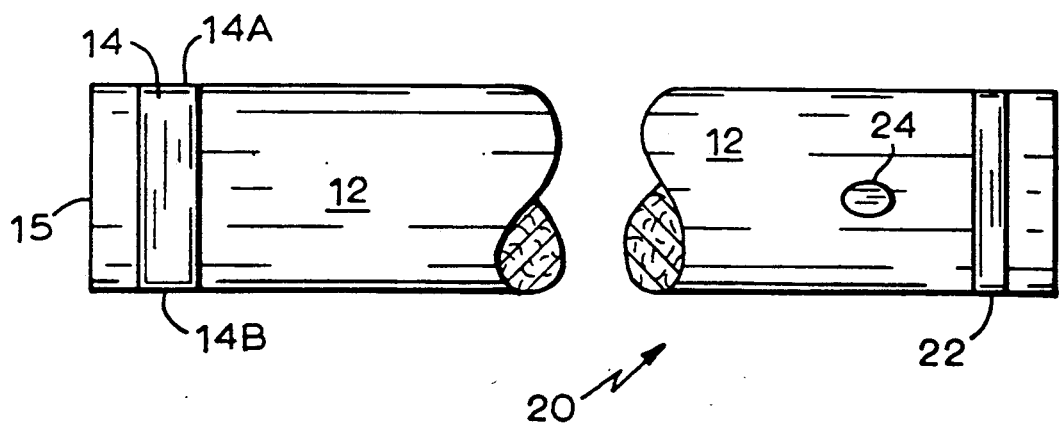
FIG. 2 is an illustration of a dispenser constructed in accordance with a second embodiment of the invention.

FIG. 2 illustrates a dispenser 20 constructed in accordance with a second embodiment of the invention. The dispenser 20 has substantially linear seals 14 and 22. A third circular-seal 24 is located proximate to one end. The circumference of seal 24 is smaller than the length of either of the end seals 14 and 22. The circular-seal 24 is preferably an ultra sonic seal.

To open the dispenser 20, a user squeezes it between the seal 14 and the seal 24. When the user squeezes with sufficient force, the dispenser wall ruptures, or opens at seal 24. The vessel fails at seal 24 before it does at either of the linear seals 14 and 22 because the forces in the interior of the vessel are focused at seal 24.

The seal 24 may be of any shape, for example, a star or a square, as long as its circumferential length is smaller than the lengths of either seal 14 or 16. The ratios of the lengths of the seals 14 and 22, respectively, and circumference of the seal 24 affect how much force a user must apply to the dispenser 20 in order to open it. If the ratios are large, the user need only apply a relatively small force to open the dispenser 20. However, if the ratios are small, the user must apply a larger force.

Figure 3:
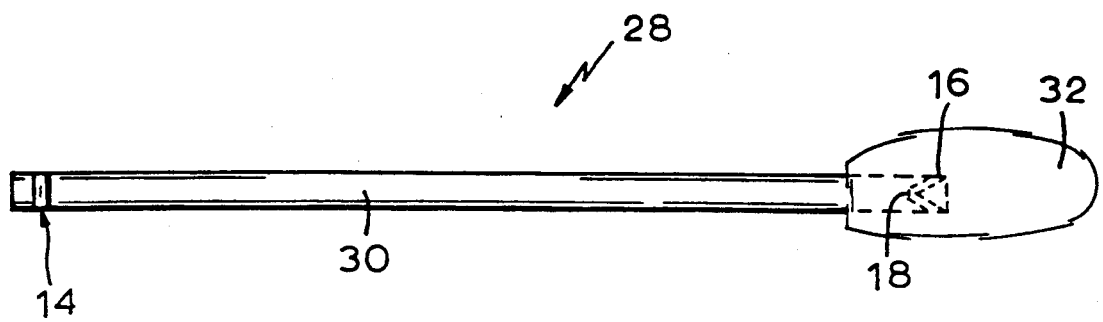
FIG. 3 is an illustration of the dispenser of FIG. 1 with a saturable covering on one end.

FIG. 3 is an illustration of an applicator 28. The applicator 28 consists of two attached pieces, a dispenser 30 which is identical to the dispenser 10 of FIG. 1 or the dispenser 20 of FIG. 2 and a saturable end-piece 32. The saturable end-piece 32 may be made out of cotton or other saturable material. In the preferred embodiment, the applicator 28 includes a dispenser 30 which is identical to dispenser 10 of FIG. 1.

To use the applicator 28, a user squeezes the dispenser 30 at a spot between the two seals 14 and 16. As discussed above with reference to FIG. 1, the dispenser 30 opens at apex 18 of the inverted V-shaped seal 16. The user continues squeezing the dispenser 30 until the fluid in the dispenser 30 saturates end-piece 32, or a portion of it. The user may then spread the fluid on a surface by rubbing the surface with the applicator end-piece 32. If the user requires additional fluid, he or she may continue to squeeze the dispenser 30 as he or she is rubbing the applicator end-piece 32 over the surface. Thus the user can apply a desired amount of fluid to a surface without contacting the fluid. Accordingly, the applicator 28 may be used to apply a sterile dosage of cream to the body, or to apply a chemical to a particular surface.

The dispensers 10 and 20 and the applicator 28 have countless uses. One specific use is in conjunction with a chemical detection kit which is the subject of a co-pending application Ser. No. 07/358,556 entitled "Chemical Detection Kit", which is assigned to the same assignee as the current invention. The chemical detection kit is used to test substances for traces of a particular chemical, for example, to test paint for traces of lead.

The kit consists of a transparent, partially sealed pouch containing a porous swatch. The swatch is impregnated with a sensing chemical, in this case one that is sensitive to lead. To test a paint sample, a user introduces paint particles into the pouch and manipulates the pouch to bring the particles into contact with the swatch. The user then applies an activating agent, for example, water, to the pouch to activate the sensing chemical. Next, the user manipulates the pouch to soak the particles and the swatch. If the particles contain lead, the swatch turns a tell-tale color.

The co-pending application discusses using an eye dropper to supply the activating agent to the pouch. If water is used as the activating agent and the local water contains traces of lead, the water contaminates the test. To avoid contaminating the tests, lead-free water housed in dispensers 10 or 20 may be included in the kits. Similarly, for the convenience of the user when other activating agents are used, the activating agents may be included in the kits in dispensers 10 or 20.

If the activating agent is included in the kit in a dispenser 10, the user simply inserts the dispensing end 17 of the dispenser 10 into the pouch containing the paint particles. The user then squeezes the dispenser 10 to open it, and continues squeezing to deliver the desired amount of activating agent to the pouch. The predictable way in which the dispenser 10 opens and dispenses the fluid enables a user to control the amount of fluid supplied to the test pouch.

An applicator 28 containing a sensing chemical may be used to test for traces of a particular substance, for example, lead, in minute particles such as the dust which results from the sanding of a painted surface. The user wipes the dry applicator end-piece 32 along a surface supporting the dust, for example, along the floor, to pick-up the dust. The user next squeezes the dispenser 30 to open it and release the sensing chemical. If the dust contains lead, the end-piece 32 turns a tell-tale color when the released chemical contacts the dust. Thus particles which are too tiny to load into a test pouch may be tested using the applicator 28.

Figure 4:
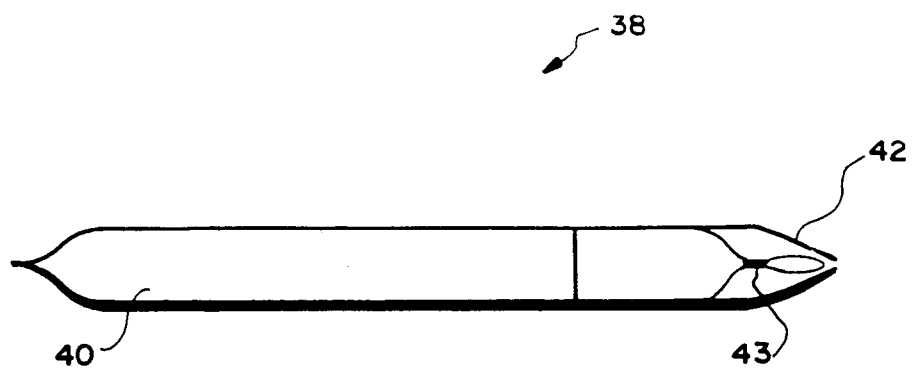
FIG. 4 is an illustration of the dispenser of FIG. 3 with an attached shield.

FIG. 4 depicts a dispenser 38 which may be the same as either dispenser 10 or 20 described above. The end of the fluid containing dispenser at which the force-focusing seal is located supports a shield 42 for directing in a particular direction fluid released from the dispenser. The shield thus directs fluid released from the vessel in the direction of the arrows. The shield may have any shape, as long as it directs the fluid in the desired direction. The shield 42 is particularly useful for directing thin fluids, which have a tendency to squirt out of the vessel when it opens.

Figure 5:
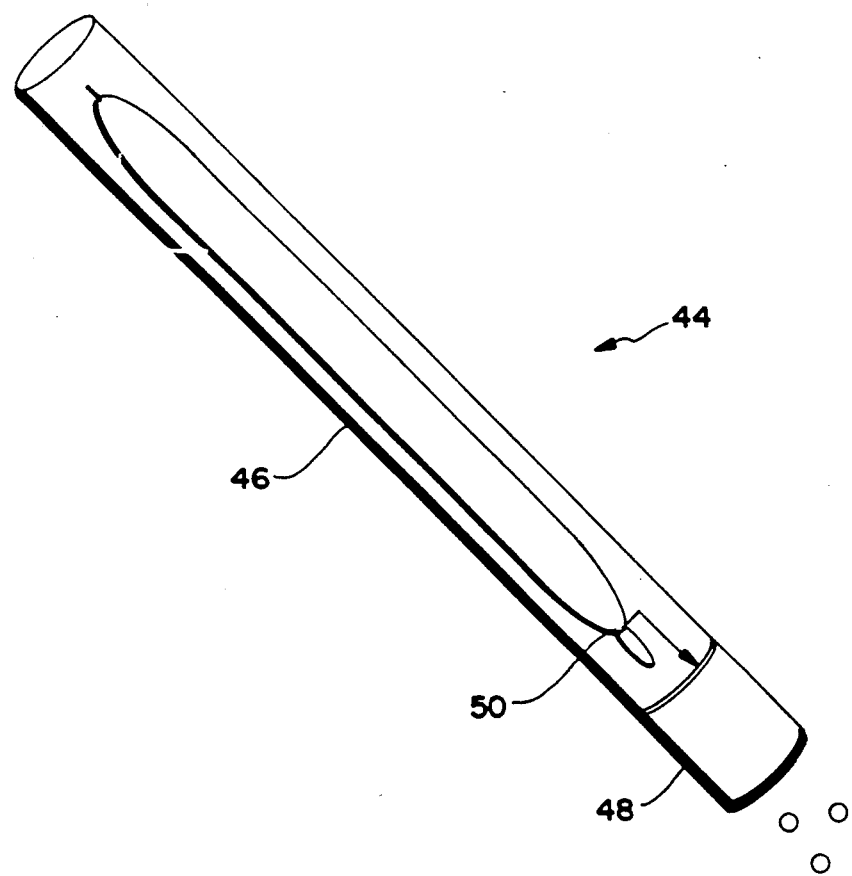
FIG. 5 is an illustration of another embodiment of a dispenser with a shield.

FIG. 5 depicts a dispenser 44 which is surrounded by a cylindrical shield 46. The dispenser 44 has at one end a protruding swab 48 which absorbs the fluid released from the dispenser 44. This dispenser may be used, for example, in an alternative arrangement of the lead test kit described above. Accordingly, swab 48 carries a sensing chemical required to test paint particles and the dispenser 44 contains an activating agent which reacts with the sensing chemical to turn it a tell-tale color in the presence of lead.

A user first picks up paint particles using the protruding swab 48. Next, the user squeezes the shield 46, and thereby applies pressure to the dispenser 44, causing the dispenser 44 to rupture at the seal 50. The dispenser 44 then releases the activating agent, and the shield 42 directs the released fluid to swab 48. When the swab 48 saturates, the activating agent reacts with the sensing chemical. If the paint particles picked up by the swab 48 contain lead, they turn the swab 48 the tell-tale color. The dispenser, swab and shield arrangement enables a user to release the activating agent in a controlled manner, without risk of contamination or leakage.

The foregoing description has been limited to a number of specific embodiments of this invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed as new and desired to be secured by Letters Patent of the United States is:

1. A fluid dispenser, the dispenser including a flexible vessel for containing a fluid, the vessel including:
   A. a top wall and a bottom wall,
   B. means comprising a seal for concentrating in a region thereof forces resulting from pressure generated in the fluid by applying a force to the vessel, said seal sealing the top wall to the bottom wall; and
   C. a shield for directing released fluid in a desired direction, said vessel being sufficiently strong that a weaker of the top wall or the bottom wall at the seal ruptures at the region of concentration in response to the applied force to form an opening through which the fluid is dispensed.

2. The fluid dispenser of claim 1, wherein the seal is V-shaped with its apex pointing toward the center of the vessel, the apex of the seal being the region of concentration.

3. The fluid dispenser of claim 1, wherein the seal is a circular seal with a periphery which is smaller than the diameter of the vessel at the location of the seal, the edge of the circular seal being the region of concentration.

4. A fluid dispenser, the dispenser including a flexible vessel for containing a fluid, the vessel including
   i. a top wall and a bottom wall, and
   ii. means comprising a seal for concentrating in a region thereof forces resulting from pressure generated in the fluid by applying a force to the vessel, said seal sealing the top wall to the bottom wall, said seal being formed ultra-sonically, and said vessel being sufficiently strong that a weaker of the top wall or the bottom wall at the seal ruptures at the region of concentration in response to the applied force to form an opening through which the fluid is dispensed.

5. The fluid dispenser of claim 4, wherein the seal is V-shaped with its apex pointing toward the center of the vessel, the apex of the seal being the region of concentration.

6. The fluid dispenser of claim 4, wherein the seal is a circular seal with a periphery which is smaller than the diameter of the vessel at the location of the seal, the edge of the circular seal being the region of concentration.

7. The fluid dispenser of claim 5, wherein said dispenser further includes a shield for directing released fluid in a desired direction.

8. The fluid dispenser of claim 6, wherein said dispenser further includes a shield for directing released fluid in a desired direction.

9. The fluid dispenser of claim 4, wherein the dispenser further includes a fluid-absorbing applicator for topically applying the contents of the vessel to a surface, the applicator being situated so as to absorb the contents of the vessel as they flow through the opening in the vessel wall.

10. A fluid dispenser, the dispenser including a flexible vessel for containing a fluid, the vessel having a seal which is formed ultra-sonically sealing a top wall to a bottom wall, the seal being V-shaped to concentrate at the apex of the seal forces resulting from pressure generated in the fluid by applying a force to the vessel, said vessel being sufficiently strong that a weaker of the top wall or the bottom wall at the seal apex ruptures in response to the applied force to form an opening through which the fluid is dispensed.

11. A fluid dispenser, the dispenser including a flexible vessel for containing a fluid, the vessel having a seal which is formed ultra-sonically sealing a top wall to a bottom wall, the seal being circular in shape with a periphery which is smaller than the diameter of the vessel, said seal concentrating at the seal forces resulting from pressure generated in the fluid by applying a force to the vessel, and being sufficiently strong that a weaker of the top wall or the bottom wall at the seal ruptures in response to the applied force to form an opening through which the fluid is dispensed.

* * * * *